(12) United States Patent
Hough et al.

(10) Patent No.: US 6,261,522 B1
(45) Date of Patent: Jul. 17, 2001

(54) SPECTROPHOTOMETRIC APPARATUS WITH REAGENT STRIP DETECTION

(75) Inventors: David Hough, Edwardsburg, MI (US); Willis E. Howard, III, Elkhart, IN (US); Richard Hurtle, Elkhart, IN (US); Gary E. Rehm, Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/170,271

(22) Filed: Oct. 13, 1998

(51) Int. Cl.⁷ .................... G01N 21/13; G01N 35/02
(52) U.S. Cl. .................... 422/82.05; 422/63; 422/65; 422/66; 422/82.08; 436/43; 436/44; 436/46; 436/47; 436/164; 436/169; 356/445; 356/446; 356/222; 356/425
(58) Field of Search .................... 422/63, 64, 65, 422/67, 68.1, 82.05, 82.08; 436/43, 44, 164, 169; 356/39, 40, 402, 408, 421, 422, 425, 445, 446

(56) References Cited

U.S. PATENT DOCUMENTS

| | | | |
|---|---|---|---|
| 3,526,480 | * 9/1970 | Findl et al. | 23/253 |
| 3,873,273 | * 3/1975 | Moran et al. | 23/253 R |
| 3,907,503 | 9/1975 | Betts et al. | 23/253 R |
| 4,539,182 | * 9/1985 | Johnson et al. | 422/99 |
| 4,689,202 | 8/1987 | Khoja et al. | 422/65 |
| 4,717,546 | * 1/1988 | Barnett | 422/63 |
| 4,755,058 | 7/1988 | Shaffer | 356/408 |
| 4,798,703 | * 1/1989 | Minekane | 422/65 |
| 4,820,491 | 4/1989 | Khoja et al. | 422/63 |
| 4,867,946 | * 9/1989 | Gross et al. | 422/68 |
| 5,028,139 | 7/1991 | Kramer et al. | 356/446 |
| 5,055,261 | 10/1991 | Khoja et al. | 422/64 |
| 5,059,394 | 10/1991 | Phillips et al. | 422/68.1 |
| 5,143,694 | * 9/1992 | Schafer et al. | 422/65 |
| 5,165,078 | 11/1992 | Hough et al. | 359/233 |
| 5,231,576 | 7/1993 | Suzuki et al. | 364/413.09 |
| 5,246,858 | 9/1993 | Arbuckle et al. | 436/8 |
| 5,250,262 | 10/1993 | Heidt et al. | 422/64 |
| 5,272,518 | 12/1993 | Vincent | 356/405 |
| 5,408,535 | * 4/1995 | Howard, III et al. | 382/1 |
| 5,491,095 | * 2/1996 | Bepko et al. | 436/518 |
| 5,661,563 | 8/1997 | Howard et al. | 356/446 |
| 5,679,584 | * 10/1997 | Mileaf et al. | 436/533 |
| 5,701,181 | 12/1997 | Boiarski et al. | 356/446 |

* cited by examiner

*Primary Examiner*—Jill Warden
*Assistant Examiner*—Kathryn Bex
(74) *Attorney, Agent, or Firm*—Roger N. Coe; Jerome L. Jeffers

(57) ABSTRACT

An apparatus for automatically detecting the presence of a reagent strip (14) having a body fluid sample disposed thereon and for inspecting the reagent strip (14) after the presence of the reagent strip (14) is detected is provided with a detection system adapted to automatically detect the presence of a reagent strip (14) at a reagent strip receiving area (12), a light source (64 or 68) adapted to illuminate the reagent strip (14) after the presence of the reagent strip (14) at the reagent strip receiving area (12) is detected, and a detector (66 or 70) adapted to receive light from the reagent strip (14) when the reagent strip (14) is being illuminated by the light source. The detection system is provided with a light emitting apparatus (30) adapted to illuminate the reagent strip receiving area (12), a detecting apparatus (32) adapted to receive light from the reagent strip receiving area (12) while the reagent strip receiving area (12) is being illuminated by the light emitting apparatus (30) and to generate a detection signal relating to the amount of light detected from the reagent strip receiving area (12), and a circuit (120 or 144, 148) adapted to automatically determine whether a reagent strip (14) is present at the reagent strip receiving area (12) based on the magnitude of the detection signal.

14 Claims, 11 Drawing Sheets

FIG. 3
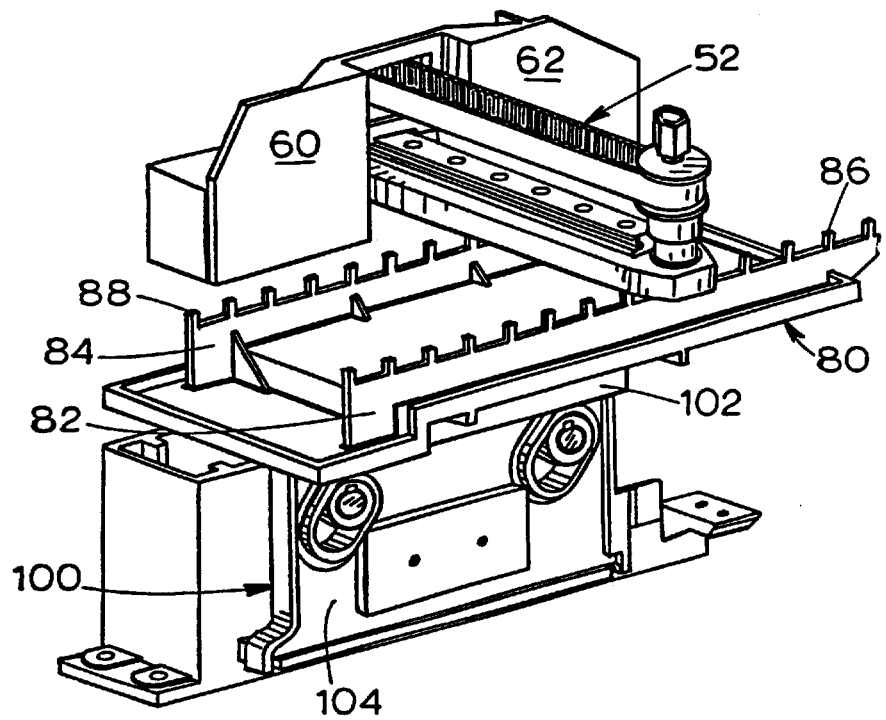
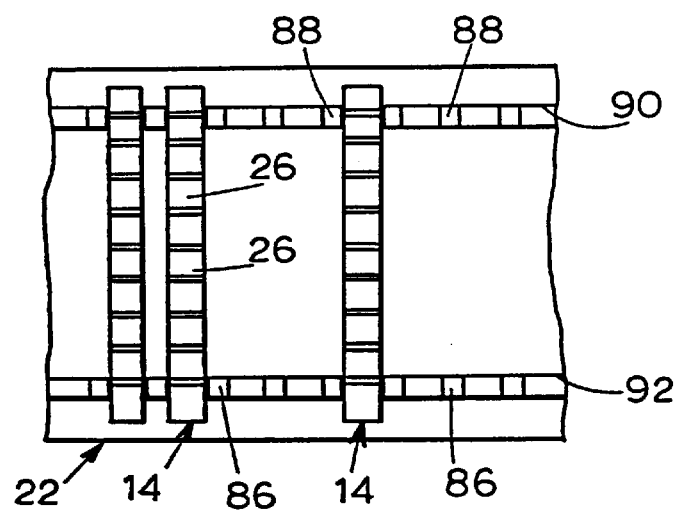
FIG. 4

SPECTROPHOTOMETRIC APPARATUS WITH REAGENT STRIP DETECTION

BACKGROUND OF THE INVENTION

The present invention relates to an apparatus and method for performing tests on a sample of body fluid to be analyzed, and more particularly to a spectrophotometer and method for the automatic detection of a reagent strip.

It is useful for various medical diagnostic purposes to utilize a spectrophotometer to analyze samples of body fluid, for example, to determine the color of a person's urine. A conventional spectrophotometer determines the color of a urine sample disposed on a white, non-reactive pad by illuminating the pad and taking a number reflectance readings from the pad, each having a magnitude relating to a different wavelength of visible light. The color of the urine on the pad may then be determined based upon the relative magnitudes of red, green and blue reflectance signals.

Conventional spectrophotometers may be used to perform a number of different urinalysis tests utilizing a reagent strip on which a number of different reagent pads are disposed. Each reagent pad is provided with a different reagent which causes a color change in response to the presence of a certain type of constituent in urine, such as leukocytes (white blood cells) or red blood cells. Such a reagent strip may have ten different types of reagent pads.

In a conventional spectrophotometer, the process of inspecting a reagent strip is performed by dipping the reagent strip in a urine sample, blotting excess urine from the reagent strip, placing the reagent strip at a designated location in the spectrophotometer, and pressing a start button which causes the spectrophotometer to begin automatic processing and inspection of the reagent strip.

U.S. Pat. No. 4,689,202 to Khoja, et al. discloses a reagent test strip reading instrument that has an area in which reagent strips may be placed and a blotter arm 108 that automatically moves reagent strips, one at a time, from the placement area towards an inspection area. As described in column 11 of the Khoja, et al. patent, the automatic movement of the blotter arm 108 is synchronized to the periodic movement of a strip advancing member 116.

In a prior art reagent strip reading instrument marketed by the assignee of this patent under the name "Clinitek 200," which instrument was designed generally in accordance with the disclosure of the Khoja, et al. patent, the blotter arm periodically swept across the area on which reagent strips were placed at a rate of about once every ten seconds, regardless of whether or not a reagent strip was present, and the instrument would generate an audible beep once for every sweep of the blotter arm. If no reagent strips were placed in the placement area after about two minutes, the blotter arm would cease its automatic movement. Thereafter, to again initiate the automatic movement of the blotter arm, the user would have to manually press a start button.

SUMMARY OF THE INVENTION

In one aspect, the invention is directed to an apparatus for automatically detecting the presence of a reagent strip having a body fluid sample disposed thereon and for inspecting the reagent strip after the presence of the reagent strip is detected. The apparatus includes a detection system adapted to automatically detect the presence of a reagent strip at a reagent strip receiving area, a light source adapted to illuminate the reagent strip after the presence of the reagent strip at the reagent strip receiving area is detected, and a detector adapted to receive light from the reagent strip when the reagent strip is being illuminated by the light source. The detection system is provided with a light emitting apparatus adapted to illuminate the reagent strip receiving area, a detecting apparatus adapted to receive light from the reagent strip receiving area while the reagent strip receiving area is being illuminated by the light emitting apparatus and to generate a detection signal relating to the amount of light detected from the reagent strip receiving area, and a circuit adapted to automatically determine whether a reagent strip is present at the reagent strip receiving area based on the magnitude of the detection signal.

The light emitting apparatus may be provided in the form of a plurality of light emitting diodes spaced to illuminate separate portions of the reagent strip receiving area, and the light detecting apparatus may include a plurality of light detectors spaced to detect light from a plurality of separate portions of the reagent strip receiving area. The light emitting apparatus may be adapted to sequentially illuminate different portions of the reagent strip receiving area at different times, and the light emitting apparatus may also be adapted to illuminate a reagent strip receiving area having a width at least about five times the width of a reagent strip.

The detection circuit, which may be in the form of a controller, may be adapted to automatically determine whether a reagent strip is present at the reagent strip receiving area based on a comparison of the magnitude of the detection signal with a threshold.

The invention is also directed to an apparatus for automatically processing a reagent strip having a body fluid sample disposed thereon which is provided with a detection system adapted to automatically detect the presence of a reagent strip at a reagent strip receiving area and a memory which stores signals relating to the amount of light detected from the reagent strip after the reagent strip is detected at the reagent strip receiving area. The detection system includes a light emitting apparatus adapted to illuminate the reagent strip receiving area, a detecting apparatus adapted to receive light from the reagent strip receiving area while the reagent strip receiving area is being illuminated by the light emitting apparatus and to generate a detection signal relating to the amount of light detected from the reagent strip receiving area, and a circuit adapted to automatically determine whether a reagent strip is present at the reagent strip receiving area based on the magnitude of the detection signal.

The apparatus may also include a conveyor system adapted to automatically move the reagent strip from the reagent strip receiving area to a reagent strip inspection location after the presence of the reagent strip is automatically detected by the circuit. The conveyor system may include a laterally moving arm which makes contact with a side of the reagent strip to force the reagent strip from the reagent strip receiving area towards the reagent strip inspection location.

In another aspect, the invention is directed to a method of automatically processing a reagent strip having a body fluid sample disposed thereon which includes the steps of: (a) automatically detecting the presence of a reagent strip at a reagent strip receiving area; (b) after the presence of the reagent strip is automatically detected in the step (a), automatically moving the reagent strip to a reagent strip inspection location; (c) illuminating the reagent strip when the reagent strip is at the reagent strip inspection location; (d) detecting light received from the reagent strip when the reagent strip is being illuminated in the reagent strip inspection position and generating illumination signals therefrom; and (e) storing signals relating to the illumination signals in a memory.

Step (a) may include the steps of: (a1) illuminating a first portion of the reagent strip receiving area at a first time; (a2) detecting light received from the first portion of the reagent strip receiving area while the first portion of the reagent strip receiving area is illuminated during the step (a1); (a3) illuminating a second portion of the reagent strip receiving area at a second time; and (a4) detecting light received from the second portion of the reagent strip receiving area while the second portion of the reagent strip receiving area is illuminated during the step (a3).

Step (a) may also include the steps of: (a1) illuminating a portion of the reagent strip receiving area; (a2) detecting light from the portion of the reagent strip receiving area while the portion of the reagent strip receiving area is being illuminated during the step (a1) and generating an illumination signal having a magnitude corresponding to the amount of light detected; and (a3) comparing the illumination signal with a threshold to determine whether the reagent strip is present at the portion of said reagent strip receiving area.

The automatic detection of the reagent strip is advantageous since the conveyor system, which may be in the form of a transfer arm, may automatically transfer the recently placed reagent strip from the receiving area towards the inspection area only when a reagent strip is present, thus eliminating the need for the transfer arm to continuously sweep the receiving area, regardless of whether a reagent strip is present, which may annoy users of the apparatus.

The features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 3 is a perspective view of an internal mechanical portion of the spectrophotometer of FIG. 1;

FIG. 4 is a top view of a reagent strip tray shown in perspective in FIG. 3;

DETAILED DESCRIPTION OF A PREFERRED EMBODIMENT

Figure 1:
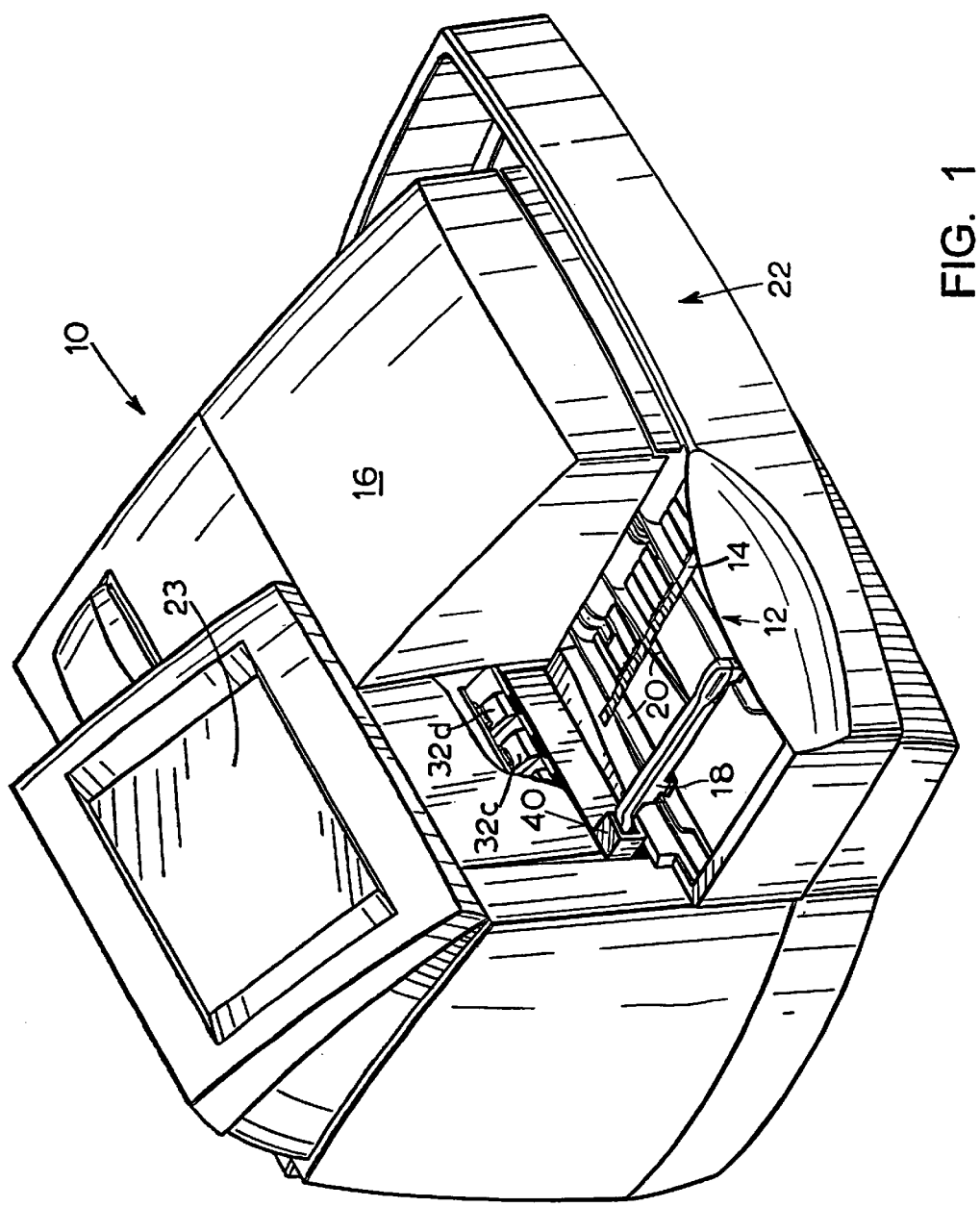
FIG. 1 is a perspective view of a spectrophotometer which may be used to perform various tests of a body fluid sample disposed on a reagent strip.

FIG. 1 illustrates a spectrophotometer 10 for performing various tests, such as urinalysis tests, on reagent strips. The spectrophotometer 10 has a receiving area 12 at which a reagent strip 14 may be placed and a reagent strip inspection area covered by a housing portion 16. The reagent strip receiving area 12 is located between a laterally movable transfer arm 18 and the left side of the housing portion 16. The reagent strip 14 is supported by a number of relatively thin wall portions 20 formed in the left-hand side of a reagent strip support table 22.

To operate the spectrophotometer 10, the reagent strip 14 may be placed anywhere in the receiving area 12. The spectrophotometer 10 automatically detects the presence of the reagent strip 14, and upon such detection, causes the transfer arm 18 to move from left to right in FIG. 1, thus automatically moving the reagent strip 14 from the receiving area 12 to the inspection area located within the housing portion 16. The spectrophotometer 10 includes a visual display 23 for displaying various messages relating to the operation of the spectrophotometer 10.

Figure 6:
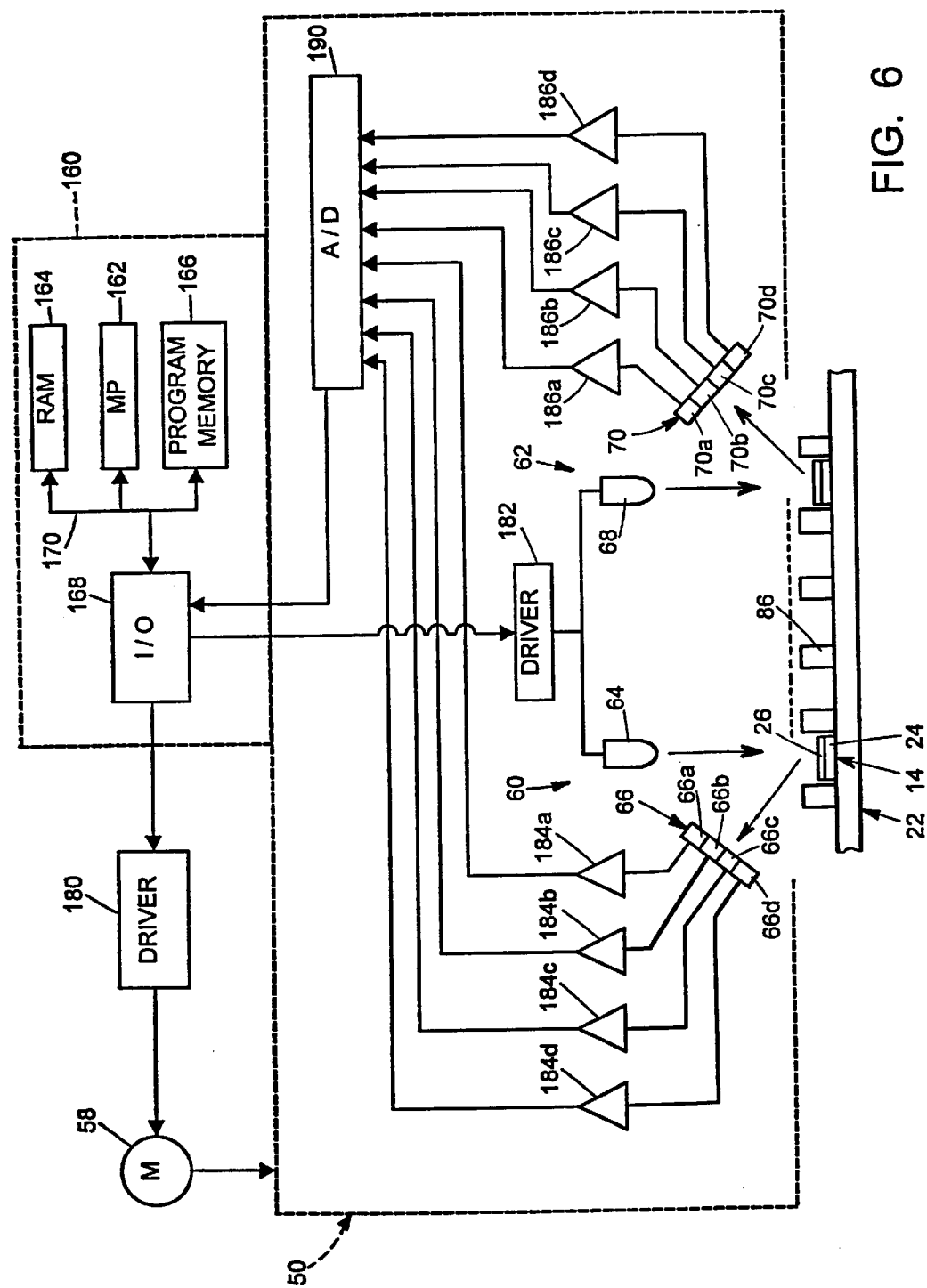
FIG. 6 is a block diagram of a second electronics portion of the spectrophotometer of FIG. 1.

As shown in FIGS. 1, 4 and 6, the reagent strips 14 used in the spectrophotometer 10 have a thin, non-reactive substrate 24 on which a number of reagent pads 26 are fixed. Each reagent pad 26 is composed of a relatively absorbent material impregnated with a respective reagent, each reagent and reagent pad 26 being associated with a particular test to be performed. When urinalysis tests are performed, they may include, for example, a test for leukocytes in the urine, a test of the pH of the urine, a test for blood in the urine, etc. When each reagent pad 26 comes into contact with a urine sample, the pad changes color over a time period, depending on the reagent used and the characteristics of the urine sample. The reagent strip 14 may be, for example, a Multistix® reagent strip commercially available from Bayer Corporation.

Mechanical Structure

Figure 2:
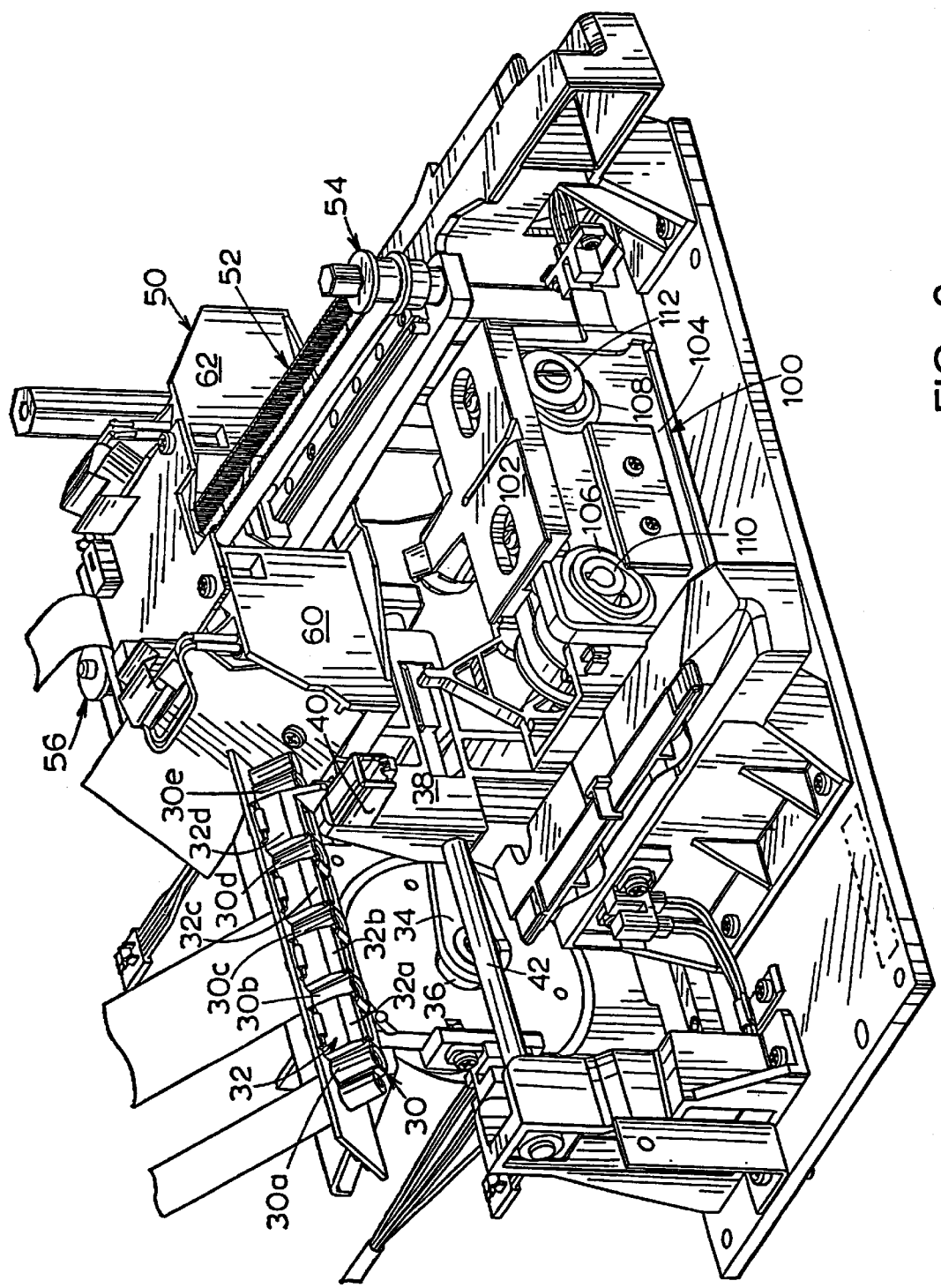
FIG. 2 is a perspective view of an internal mechanical portion of the spectrophotometer of FIG. 1.

FIG. 2 is a perspective view of the interior mechanical structure of the spectrophotometer 10. Referring to FIG. 2, the spectrophotometer 10 includes a light emitting apparatus 30, which may be provided in the form of five light-emitting diodes (LEDs) 30a–30e, which may be in the form of narrow angle, high output LEDs commercially available from Hewlett Packard. The LEDs 30a–30e may be spaced apart so that each of them illuminates a separate portion of the reagent strip receiving area 12. The spectrophotometer 10 includes a detecting apparatus 32, which may be in the form of four light detectors 32a–32d, each of which is disposed between two of the LEDs 30a–30e. The detectors 32a–32d are positioned so that they detect light which is received from portions of the receiving area 12 which are illuminated by the LEDs 30a–30e.

As shown in the left-hand portion of FIG. 2, the spectrophotometer 10 includes a pivot arm 34 having a central portion which is connected to a rotatable shaft 36, which is controllably driven by a motor (not shown). The end of the pivot arm 34 is slidably disposed in a vertical shaft formed in the back of a transfer arm support member 38 to which the transfer arm 18 (FIG. 1) is connected. The transfer arm support member 38, which has a receptacle 40 in which an end of the transfer arm 18 is disposed, is slidably supported by a horizontally disposed cylindrical rod 42. The horizontal position and movement of the transfer arm 18 is controlled by selectively causing the pivot arm 34 to rotate about the central shaft 36 to change the lateral position of the end of the pivot arm 34, and thus the lateral position of the transfer arm support member 38.

As shown in the right-hand portion of FIG. 2, the spectrophotometer 10 has a movable carriage 50 that is fixed to one side of a positioning belt 52 supported by a pair of toothed gears 54, 56. The gear 56 is fixed to a rotatable drive shaft (not shown) that is controllably driven by a motor 58 (FIG. 6) to precisely move and position the movable carriage 50 in a direction parallel to the length of the reagent strip 14 (FIG. 1). Although a positioning system in the form of gears 54, 56 and belt 52 is shown, other types of positioning systems could be utilized, such as one or more round gears which mate with a linear gear fixed to the readheads 60, 62, or any type of positioning system adapted to adjust the linear position of a device.

The movable carriage 50 has a pair of readheads 60, 62. The readhead 60 includes a light source 64 (FIG. 6), which may be provided in the form of an incandescent lamp, for example, and a detector 66, which may be provided in the form of four light detectors 66a–66d, each of which is adapted to detect light of a different wavelength, such as red, blue, green and infrared light, for example. The readhead 62 includes a light source 68 (FIG. 6), which may be provided in the form of an incandescent lamp, and a detector 70, which may be provided in the form of four light detectors 70a–70d, each of which is also adapted to detect light of a different wavelength. Although the readheads 60, 62 could be designed as disclosed in U.S. Pat. No. 5,661,563 to Howard, et al., which is incorporated by reference herein, no particular design of the readheads 60, 62 is considered necessary to the invention. The light sources 64, 68 could be other than incandescent light sources, and the detectors 66, 70 could be designed to detect light of only a single wavelength.

FIG. 3 is a perspective view of a portion of the spectrophotometer 10 which shows a reagent strip advancing tray 80. The advancing tray 80 has a pair of upwardly extending walls 82, 84. The upper portion of the wall 82 has a plurality of pegs 86 extending therefrom, and the upper portion of the wall 84 has a plurality of pegs 88 extending therefrom. The pegs 86, 88 are spaced apart by a distance slightly greater than the width of the reagent strip 14 so that the space between each adjacent pair of pegs 86, 88 can accommodate one of the reagent strips 14. Referring to FIG. 4, the pegs 86, 88 of the advancing tray 80 may extend upwardly through a pair of slots 90, 92 formed in the reagent strip support table 22.

The reagent strip advancing tray 80 is supported by a positioning mechanism 100 which is shown in FIGS. 2 and 3. The positioning mechanism 100 has a support table 102 which supports the reagent strip advancing tray 80 and a mechanism for moving the support table 102 in a generally circular path which includes a vertical member 104 having a pair of oblong slots 106, 108 formed therein and a pair of motor-driven actuators 110, 112 disposed within the slots 106, 108. Rotation of the actuators 110, 112 causes the vertical member 104 and the support table 102 to move in a circular path, as disclosed in U.S. Pat. No. 4,689,202, which is incorporated by reference herein.

The movement of the support table 102 causes the advancing tray 80 to move in a circular path, which in turn moves the pegs 86, 88 to cause the reagent strips 14 disposed between them to be periodically moved or indexed rightward through the spectrophotometer 10, so that a reagent strip 14 is disposed at a first reagent strip inspection position beneath the readhead 60, and then is disposed at a second reagent strip inspection position beneath the readhead 62.

Referring to FIG. 4, when the advancing tray 80 moves in a single circular path, the pegs 86, 88 move from left to right while they extend upwardly through the reagent strip support table 22, thus moving each of the reagent strips 14 one reagent strip position to the right. During the latter half of the circular motion, the pegs 86, 88 are downwardly retracted so that their upper ends are disposed beneath the upper surface of the support table 22, so that they can be moved from right to left without moving the reagent strips 14. The particular design of the system for conveying the reagent strips 14 from the receiving area 12 to the inspection area within the housing portion 16 and for conveying the reagent strips 14 within the inspection area is not considered necessary to the invention, and other types of conveyor systems could be utilized.

Electronics

Figure 5:
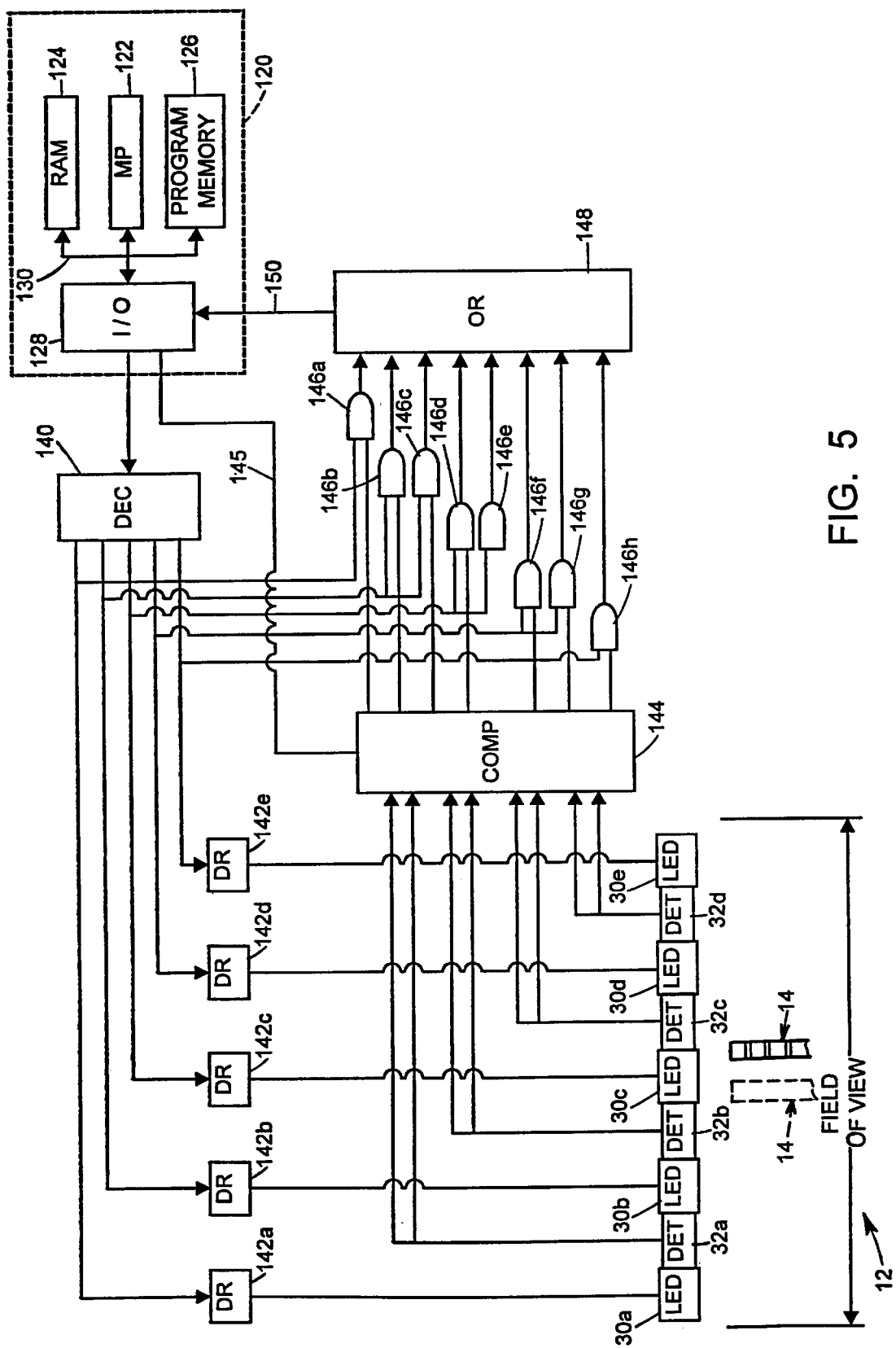
FIG. 5 is a block diagram of a first electronics portion of the spectrophotometer of FIG. 1.

FIG. 5 is a block diagram of the electronics and other components of the spectrophotometer 10 which relate to the automatic detection of a reagent strip 14 at the reagent strip receiving area 12. Referring to FIG. 5, the automatic detection of a reagent strip 14 is controlled by a controller 120 which has a microprocessor 122, a random-access memory (RAM) 124, a program memory 126, and an input/output (I/O) circuit 128, all of which are interconnected via an address/data bus 130.

The controller 120 selectively applies power to the LEDs 30a–30e via a decoder circuit 140 which is connected to five driver circuits 142a–142e, each of which is connected to cause a respective one of the LEDs 30a–30e to be turned on. The LEDs 30a–30e may be turned on periodically, one at a time, so that separate overlapping portions of the reagent strip receiving area 12 are successively illuminated.

The detectors 32a–32d are positioned to detect light from separate overlapping portions of the receiving area 12, which overlapping portions generally make up the field of view of the detecting apparatus 32, as shown in FIG. 5. Each of the detectors 32a–32d generates an illumination signal having a magnitude corresponding to the amount of light detected. Each of those illumination signals is transmitted to a programmable comparator circuit 144, which compares each of the illumination signals to a respective one of eight thresholds, as described below, to determine whether a reagent strip 14 is present in the reagent strip receiving area 12. The thresholds may be transmitted to the comparator 144 via a line 145.

The comparator 144 generates eight output signals, each output signal having a value (i.e. logic "0" or logic "1") corresponding to whether the associated illumination signal was greater than its associated threshold. Those eight output signals may be provided to a selection circuit, which may be in the form of eight AND gates 146a–146h, to enable certain of the output signals and disable the rest. Only one of the five outputs of the decoder 140 is activated, or logic "1," at a time, in order to turn on exactly one of the LEDs 30a–30e at a time. Each of those five outputs is transmitted to either one or two of the AND gates 146a–146h in order to enable either one or two of the AND gates 146a–146h and to disable the rest.

In particular, a logic "0" output of the decoder 140, will force the output of the AND gate(s) to which it is supplied to have a logic "0" value, thus preventing the detection signal(s) provided to such AND gate(s) to cause the output of the OR gate to be logic "1," representing the detection of a reagent strip 14. For example, when the LED 30a is turned on, the single logic "1" output connected to the driver circuit 142a will allow the AND gate 146a (which receives the illumination signal generated by the detector 32a) to be enabled, and the other four logic "0" outputs of the decoder 140 will effectively disable the AND gates 146b–146h.

The output signals of the AND gates 146a–146h are transmitted to an OR gate 148, which transmits a strip-detected signal to the controller 120 if any of the inputs to the OR gate 148 is logic "1," meaning that at least one of the illumination signals generated by the detectors 32a–32d was greater than its associated threshold.

The function of the circuit components 144, 146, 148 could alternatively be done by another circuit, or alternatively by a portion of a computer program performed by the controller 120.

FIG. 6 is a block diagram of the electronics and other components of the spectrophotometer 10 which relate to the inspection of reagent strips 14 at the reagent strip inspection positions within the housing portion 16. Referring to FIG. 6, the inspection of reagent strips 14 is controlled by a controller 160 which has a microprocessor 162, a random-access memory (RAM) 164, a program memory 166, and an I/O circuit 168, all of which are interconnected via an address/data bus 170.

The controller 160 selectively drives the motor 58, which may be a stepping motor, through a drive circuit 180, to position the carriage 50 so that each of the readheads 60, 62 is positioned over a respective one of the two reagent strip inspection locations (at which either one or two reagent strips 14 may be present). The controller 160 selectively turns on the light sources 64, 68 in the readheads 60, 62 via a drive circuit 182 and, while those light sources 64, 68 are turned on, receives illumination signals from eight amplifiers 184a–184d, 186a–186d, each of which is connected to receive the output of one of the detectors 66a–66d, 70a–70d. Those illumination signals are transmitted to an analog-to-digital (A/D) converter 190, which converts them from analog signals into digital signals and then transmits them to the controller 160, which causes signals relating to them to be stored in the RAM 164. The illumination signals may be stored in the RAM 164, or alternatively reflectance signals which are derived from the illumination signals may be stored in the RAM 164.

Automatic Detection of Reagent Strip

The automatic detection of a reagent strip 14 in the reagent strip receiving location 12 is controlled by a computer program stored in the program memory 126 of the controller 120 and executed by the microprocessor 122 (FIG. 5). That computer program includes a calibration routine 200 (FIG. 7) that is performed each time the spectrophotometer 10 is turned on, a strip detect routine 240 (FIG. 8) periodically performed to detect the placement of a reagent strip 14 at any point within the reagent strip receiving area 12, and a software routine 260 (FIG. 9) that automatically detects when the reagent strip 14 reaches a predetermined position between the reagent strip receiving location 12 and the reagent strip inspection area disposed beneath the housing portion 16.

Calibration Routine

Figure 7:
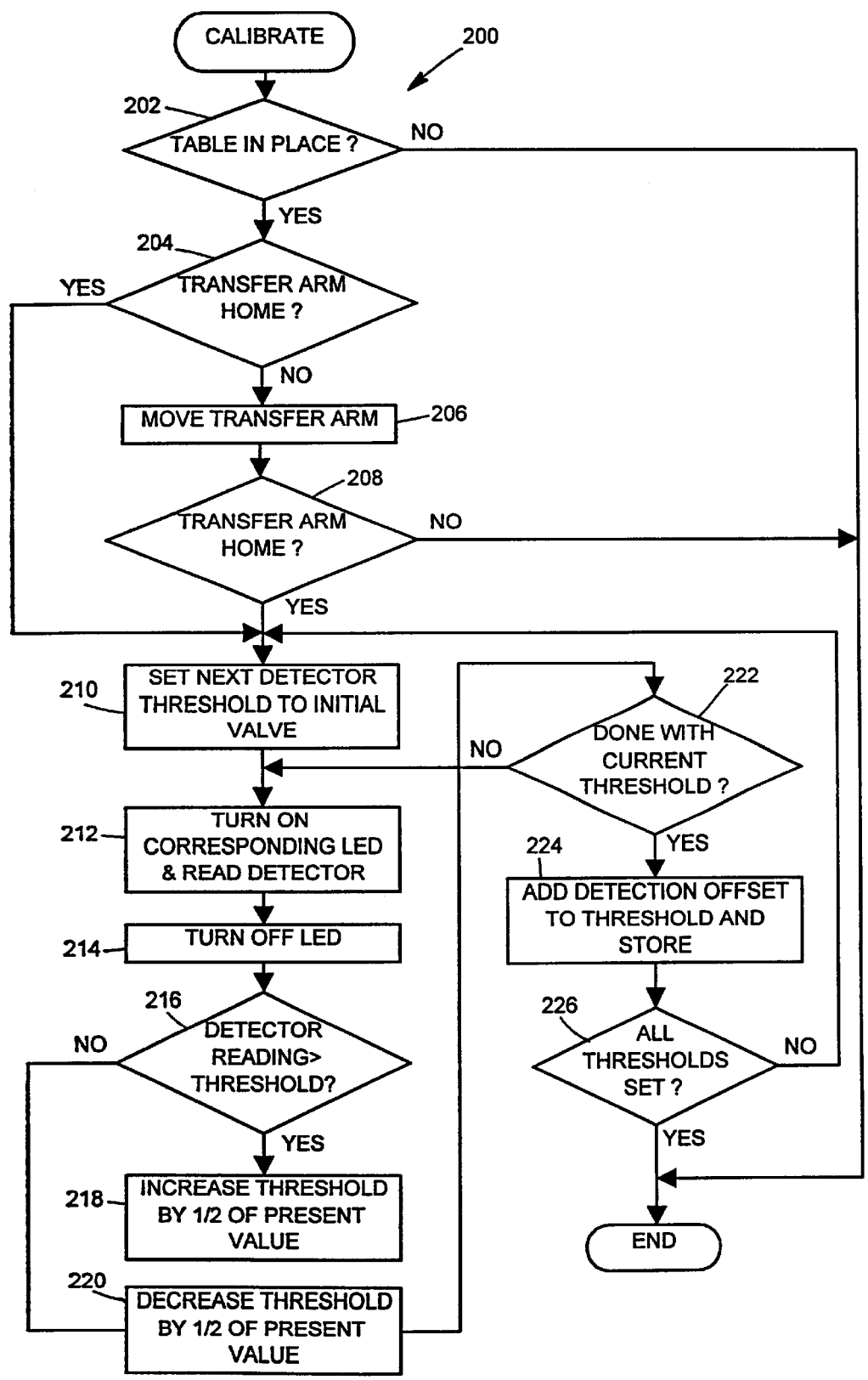
FIG. 7 is a flowchart of a calibrate software routine performed during operation of the spectrophotometer.

A flowchart of the calibration routine 200 is shown in FIG. 7. This routine 200 is performed when the spectrophotometer 10 is turned on to determine the eight thresholds used by the comparator 144 (FIG. 5) in the detection of a reagent strip 14. Referring to FIG. 7, a number of preliminary steps 202, 202, 206, 208 may be utilized to ensure that the reagent strip support table 22 (FIGS. 1 and 4), which is removable from the spectrophotometer 10, is in place and that the transfer arm 18 is at a home position and out of the field of view of the detectors 32a–32d (FIG. 5).

Each illumination signal generated by the four detectors 32a–32d used to detect the presence of a reagent strip 14 is compared with either one or two thresholds, which are determined by the routine 200. When the LED 30a disposed on the left end of the light emitting apparatus 30 is turned on, the signal generated by its adjacent detector (i.e. detector 32a) is compared with a threshold. Similarly, when the LED 30e disposed on the right end of the light emitting apparatus 30 is turned on, the signal generated by its adjacent detector (i.e. detector 32d) is compared with a threshold.

When one of the LEDs 30b–30d positioned between the LEDs 30a and 30e is turned on, the two signals generated by the two detectors disposed adjacent the powered LED are compared with two thresholds. For example, when the LED 30c is turned on, the signal generated by the detector 32b is compared with a first threshold and the illumination signal generated by the detector 32c is compared with a second threshold. This is done because a reagent strip 14 could be present at two possible locations relative to the turned on LED 30c: 1) a first location, shown in solid lines in FIG. 5, between the turned on LED 30c and the detector 32c on its right-hand side, and 2) a second location, shown in dotted lines in FIG. 5, between the turned on LED 30c and the detector 32b on its right-hand side. The reagent strip 14 is best detected in the first position via the detector 32c, and is best detected in the second position via the detector 32b.

Referring to FIG. 7, steps 210, 212, 214, 216, 218, 220, 222 and 224 are performed, without any reagent strip 14 present in the receiving area 12, to determine the eight thresholds used in the reagent strip detection process. At step 210, the next (or first) detector threshold is set to an initial value, such as 50% of the maximum range, for example. At step 212, the corresponding LED is turned on and the illumination signal generated by the associated detector is read, and at step 214 the LED is turned off (the LEDs 30a–30e may be turned on for very short time periods, such as 15 microseconds).

If the detector reading is greater than the threshold as determined at step 216, the routine branches to step 218 where the value of the threshold is increased by one-half its current value; otherwise, the routine branches to step 220 where the value of the threshold is decreased by one-half its current value. The routine then branches to step 222, which determines whether the current threshold has been finalized. This could be accomplished, for example, by performing steps 212, 214, 216, 218, 220 a predetermined number of times, such as seven times.

It should be noted that the effect of the repeated performance of even steps 212–220 is to make the threshold approximately equal to the magnitude of the illumination signal generated by the detector in the absence of a reagent strip 14.

At step 224, a detection offset is then added to the threshold determined by even steps 212–222. This detection offset is based upon the difference in the illumination signal produced by the presence of a reagent strip 14, which is white or has a relatively light color, and the color of the reagent strip support table 22, which has a relatively dark color. At step 226, if not all of the eight thresholds have been set, the routine branches back to step 210 to set the next threshold.

In the above routine, the eight thresholds are set by turning on the LEDs 30a–30e and reading their associated detectors 32a–32d as follows: 1) turning on LED 30a and reading detector 32a; 2) turning on LED 30b and reading detector 32a; 3) turning on LED 30b and reading detector 32b; 4) turning on LED 30c and reading detector 32b; 5) turning on LED 30c and reading detector 32c; 6) turning on LED 30d and reading detector 32c; 7) turning on LED 30d and reading detector 32d; and 8) turning on LED 30e and reading detector 32d. Although a particular method of calibrating the spectrophotometer 10 is described above, that particular method is not considered necessary to the invention and other methods (or no calibration method) could be used.

Strip Detect Routine

Figures 8, 9:
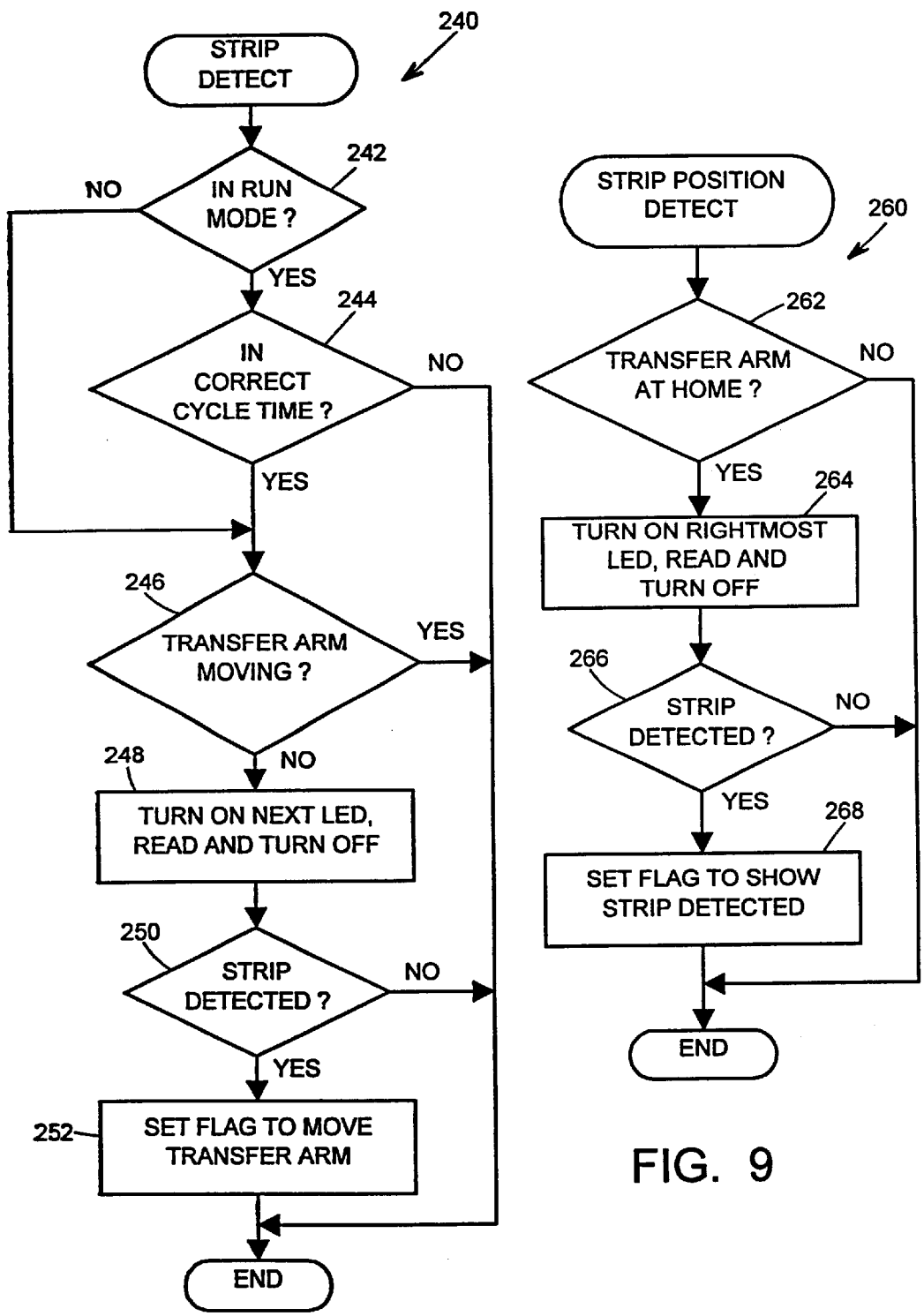
FIG. 8 is a flowchart of a strip detect software routine performed during operation of the spectrophotometer.
FIG. 9 is a flowchart of a strip position detect software routine performed during operation of the spectrophotometer.

FIG. 8 is a flowchart of the strip detect routine 240, which is periodically performed, once every 100 milliseconds for example, to determine whether a reagent strip 14 has been placed in the reagent strip receiving area 12.

Referring to FIG. 8, preliminary steps 242, 244, 246 may be performed to limit the times when the spectrophotometer 10 searches for the presence of a reagent strip 14. When the spectrophotometer 10 is in its run mode, the spectrophotometer 10 has a predetermined cycle time (e.g. seven seconds in duration) which relates to its operation. At step 242, if the spectrophotometer 10 is not in the run mode, meaning that it is not operating according to its cycle time, the routine branches to step 246. If the spectrophotometer 10 is in its run mode, the routine branches to step 244 where it determines whether the spectrophotometer 10 is in a predetermined correct portion of the cycle time during which time it is appropriate to check for the presence of a reagent strip 14. This correct cycle time may be include time periods during which the transfer arm 18 is probably not moving (it is possible that a moving transfer 18 could be mistaken for a reagent strip 14) and may exclude other time periods, for example, later periods in a cycle which would not allow sufficient time for the user to place a reagent strip 14 at the receiving location 12. If the transfer arm 18 is moving as determined at step 246, the routine ends without checking for the presence of a reagent strip 14 since the moving transfer arm 18 could be mistaken for a reagent strip 14.

At step 248, the next (or first) of the LEDs 30a–30e is turned on, the one or two of the detectors 32a–32d associated with that LED is read (via the electronics as described above), and the LED is turned off. At step 250, if the illumination signal(s) generated by the detector(s) is (are) greater than the corresponding threshold(s) (as determined by the detection signal on the line 150 generated by the OR circuit 148 described above), meaning that a reagent strip 14 is detected, the routine branches to step 252, where a flag is set to subsequently cause the transfer arm 18 to automatically move, from left to right in FIG. 1, in order to move the reagent strip 14 from the reagent strip receiving area 12 to the inspection area disposed within the housing portion 16. If no reagent strip 14 is detected, the routine simply ends.

Each time the routine 240 is performed, a successive one of the LEDs 30a–30e is turned on, and the one or two adjacent detectors 32 are read to determine whether a reagent strip 14 is present.

Strip Position Detect Routine

FIG. 9 is a flowchart of a reagent strip position detect routine 260 that may be performed to detect a reagent strip 14 as it is being moved from the receiving area 12 to the inspection area within the housing portion 16. The position detect routine 260 is periodically performed (e.g. every 3 milliseconds) while the transfer arm 18 is moving. Since the transfer arm 18 is intended to move only in response to an earlier detection of a reagent strip 14 at the receiving area 12, the routine 260 acts to confirm the presence of a reagent strip 14 at the right side of the moving transfer arm 18, and thus that the presence of a reagent strip 14 caused the transfer arm 18 to begin moving, as opposed to the unintended detection of the temporary presence of someone's hand in front of one of the detectors 32a–32d, for example.

Referring to FIG. 9, at step 262, if the transfer arm 18 is at a "home" position (which may be determined by a conventional home sensor) located adjacent the right end of the receiving area 12, steps 264, 266, 268 are performed to determine whether a reagent strip 14 is present. At step 264, the rightmost LED 30e is turned on, the rightmost detector 32d is read, and the LED 30e is turned off. At step 266, if a reagent strip 14 is detected (based on comparison of the illumination signal with the corresponding threshold), the routine branches to step 268 where a flag is set to indicate that the reagent strip 14 was detected, thus confirming the presence of the reagent strip 14. The absence of the strip detected flag being set after the routine 260 is performed a predetermined number of times when the transfer arm 18 is in the home position indicates to the spectrophotometer 10 that the initial detection of the reagent strip 14 that caused the transfer arm 18 to move was spurious.

Inspection of Reagent Strip After Detection

During operation of the spectrophotometer 10, reagent strips 14 may be continually placed at the receiving location 12 by the operator, one at a time, and such reagent strips 14 will be automatically transferred inside the housing portion 16 to be optically inspected by the readheads 60, 62 at one or both of two inspection locations, one of the inspection locations being aligned with the readhead 60 and the other inspection location being aligned with the readhead 62, as shown in FIG. 6.

The inspection of reagent strips 14 is controlled by a computer program stored in the program memory 166 of the controller 160 (FIG. 6) and executed by the microprocessor 162. That computer program includes a main routine 300 (FIG. 10) that is performed during operation of the spectrophotometer 10, an initialize position routine 310 that is periodically performed to position the readheads 60, 62 over a pair of calibration chips of a known color, a calibration routine 320 that is periodically performed while the readheads 60, 62 are positioned over the calibration chips, and a read routine 330 that is performed to inspect the reagent pads 26 of the reagent strips 14 at the inspection locations.

Main Routine

Figure 10:
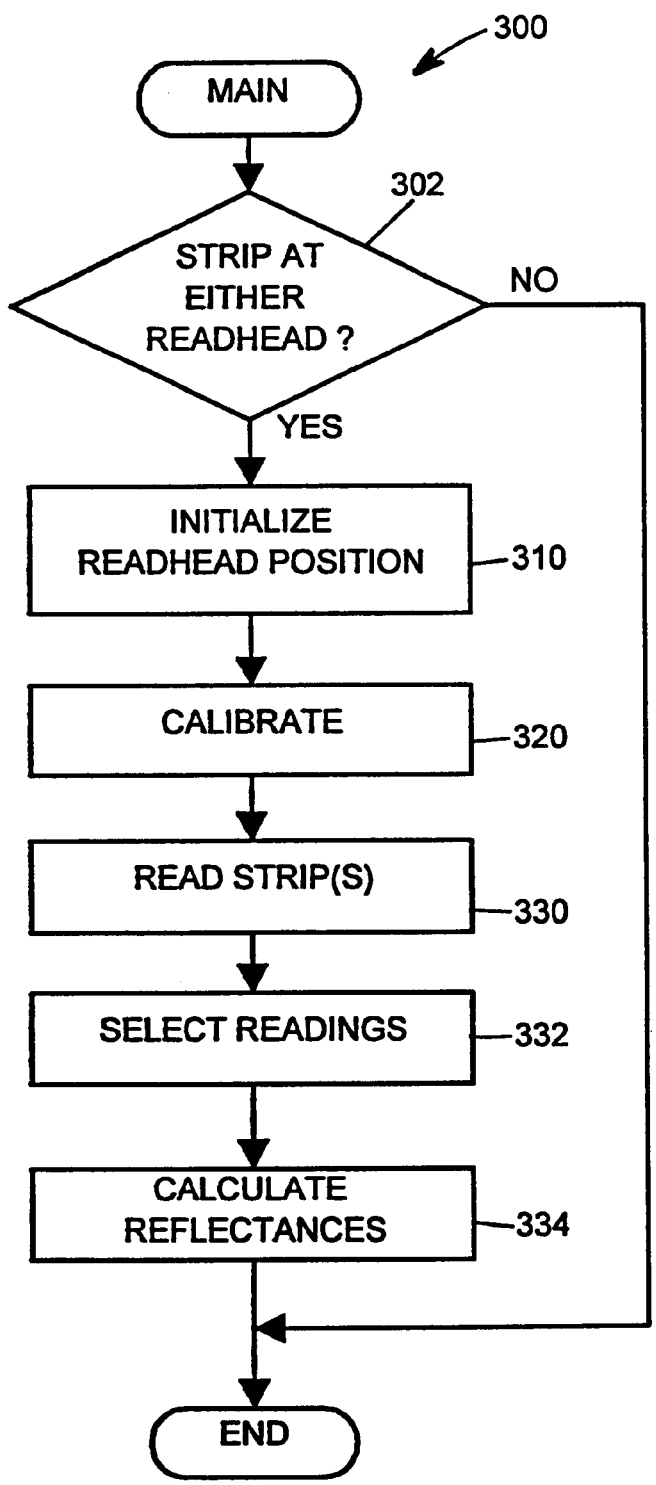
FIG. 10 is a flowchart of a main software routine performed during operation of the spectrophotometer.

Referring to flowchart of the main routine 300 shown in FIG. 10, if there is no reagent strip 14 at either of the two inspection locations as determined at step 302, the routine ends. Since the position of the reagent strips 14 may be kept track of by the controller 160 as the reagent strips 14 are fed by the transfer arm 18, the presence of a reagent strip 14 at either of the two inspection locations can be determined by the controller 160.

If there is a reagent strip 14 at one (or reagent strips 14 at both) of the inspection locations, the initialize routine 310, which causes the readheads 60, 62 to be moved to the centers of the calibration chips, is performed. The calibrate routine 320 is then performed to calibrate the detectors 66a–66d and 70a–70d of the readheads 60, 62, and then the read routine 330 causes the reagent pads 26 disposed along the length of each reagent strip 14 at an inspection location to be successively inspected by reading the illumination signals generated by the detectors 66a–66d, 70a–70d while each reagent pad 26 is illuminated by one of the light sources 64, 68.

As described below in connection with FIG. 13, the detectors 66a–66d, 70a–70d of the readheads 60, 62 are read at very close intervals, such as every 0.017 of an inch. Since the width of each of the reagent pads 26 on a reagent strip 14 is considerably wider than 0.017 of an inch, multiple sets of detector readings are generated for each reagent pad 26.

Step 332 may be performed to select which sets of the detector readings are utilized. The detector readings may be selected, for example, by determining which sets of detector readings were taken from the approximate center of each of the reagent pads 26. This could be accomplished by detecting the position of the longitudinal end of the reagent strip 14 (when the reflectance signal increases due to the detectors 66a–66d moving from the relatively dark table 22 to a relatively light reagent strip 14), and then selecting only those detector readings corresponding to predetermined distances from the end of the reagent strip 14 (based on the known widths and spacings of the reagent pads 26).

Figure 12:
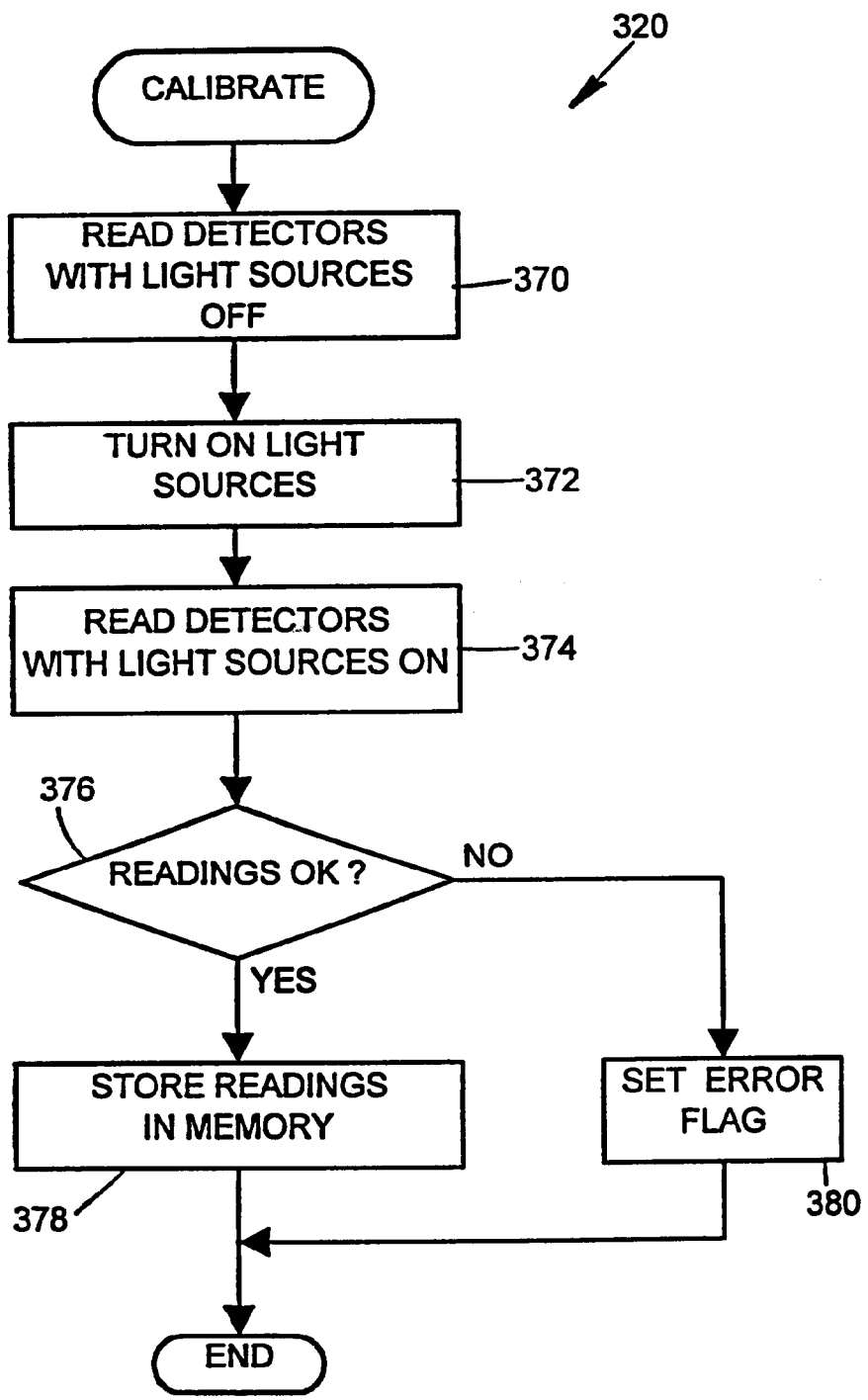
FIG. 12 is a flowchart of a calibration software routine performed during operation of the spectrophotometer.

Step 334 may be performed to transform the raw data of the detector readings into reflectance data, taking into account the dark values and the calibration values described below in connection with FIG. 12. For example, the calculated reflectance ("Reflect$_{Calc}$") could be determined in accordance with the following formula:

$$\text{Reflect}_{Calc} = \% \text{ Reflectance} * (\text{Reagent} - \text{Dark}) / (\text{Calibration} - \text{Dark}),$$

where "%Reflectance" is the known reflectance percentage of the calibration chips, where "Reagent" is the raw detector reading of a reagent pad 26, and where "Dark" and "Calibration" are the dark and calibration values described below in connection with FIG. 12.

Initialize Position Routine

The purpose of the initialize position routine 310 (FIG. 11) is to position the detectors 66a–66d, 70a–70d of the readheads 60, 62 so that they are disposed over, respectively, the centers of a pair of calibration chips (not shown) of a known color which are disposed on the reagent strip support table 22.

Figure 11:
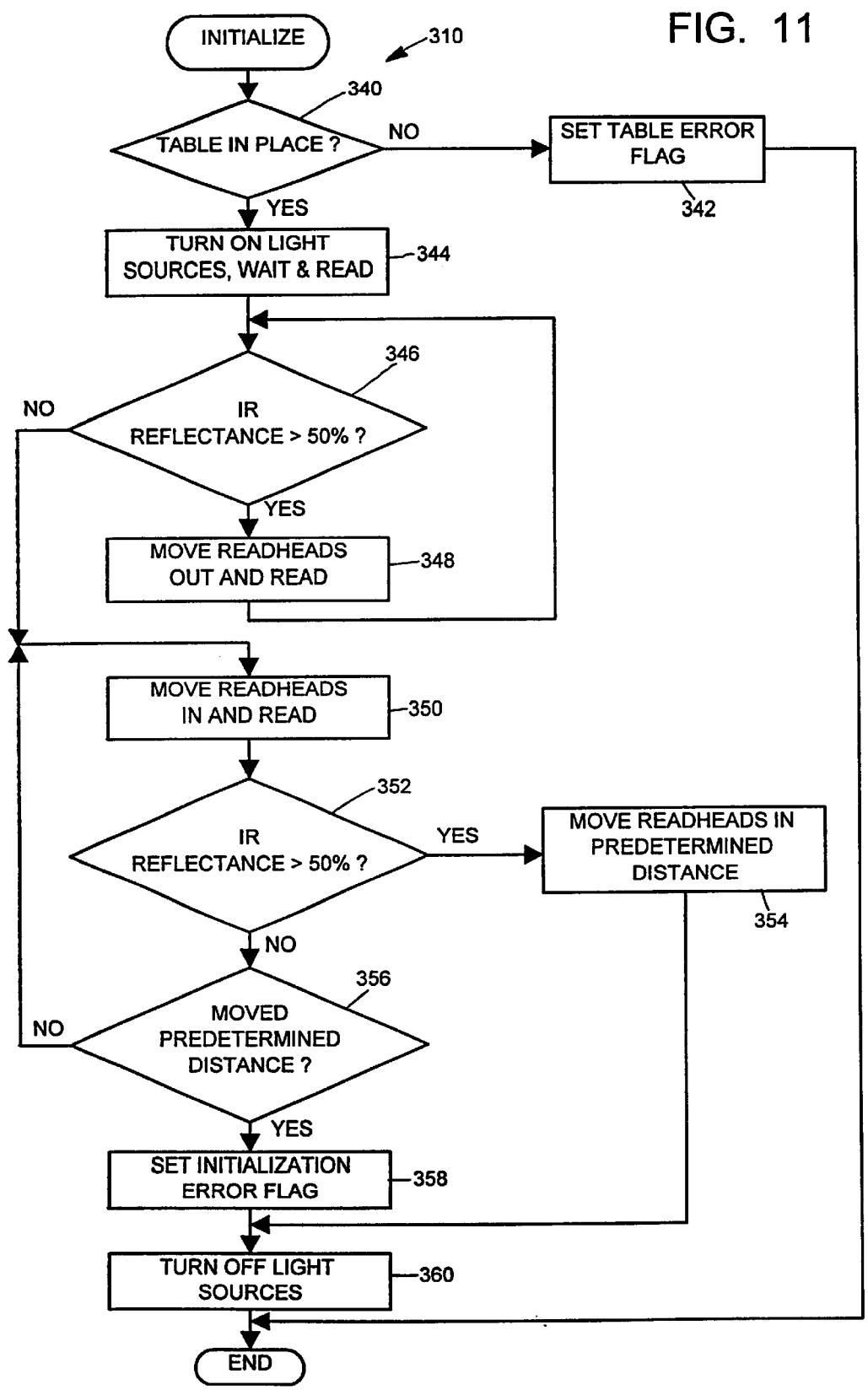
FIG. 11 is a flowchart of an initialization software routine performed during operation of the spectrophotometer.

Referring to FIG. 11, the initialize position routine 310 begins at step 340, which determines whether the reagent strip support table 22, which may be removed from the spectrophotometer 10 for cleaning purposes, is in place. If not, an error flag is set at step 342 and then the routine ends. If the table 22 is in place, the routine branches to step 344 where the light sources 64, 68 of the readheads 60, 62 are turned on, a predetermined period of time (e.g. one-half of a second) is waited, and the detectors which detect infrared (IR) radiation are read by the controller 160 (FIG. 6) via the A/D converter 190.

The purpose of even steps 346–360 is to position the readheads 60, 62 so that the detectors 66a–66d, 70a–70d are positioned over the centers of their respective calibration chips (not shown), which are relatively light in color compared with the surrounding area of the reagent strip support table 22. Thus, when the detectors 66a–66d are positioned over the calibration chips, the reflectance represented by the signals generated by the detectors 66a–66d, 70a–70d will be relatively large, e.g. over 50%.

When the routine 310 begins, the detectors 66a–66d, 70a–70d of the readheads 60, 62 are positioned somewhere over the calibration chips. The precise positioning of the detectors 66a–66d, 70a–70d over the centers of the respective calibration chips is done by steps 346 and 348, which move the readheads 60, 62 in one direction until they pass over the edges of the calibration chips (which is detected at step 346 when the percent reflectance decreases to become less than a predetermined value, such as 50%); by steps 350 and 352, which move the readheads 60, 62 back in the opposite direction until they pass over the same edges of the calibration chips (which is detected when the percent reflectance increases to become greater than a predetermined value, such as 50%), and then by step 354, which moves the readheads 60, 62 in the same direction by a predetermined distance (corresponding to one-half the length of the calibration chips) so that the detectors 66a–66d, 70a–70d are positioned directly over the centers of the calibration chips.

Step 356 checks for an error condition (the failure of the edges of the calibration chips to be detected after movement of the readheads 60, 62 a predetermined distance), which if present causes an error flag to be set at step 358, and at step 360, the light sources 64, 68 turned on at step 344 are turned off.

If the above positioning routine is utilized, it may be modified by positioning one of the readheads 60, 62 relative to one of the calibration chips and (since the readheads 60, 62 are fixed relative to one another and since the calibration chips are also fixed relative to each other) assuming that the other readhead is properly positioned over its calibration chip.

Calibration Routine

The calibration routine 320 (FIG. 12) is performed after the detectors 66a–66d, 70a–70d of the readheads 60, 62 are positioned over the centers of the calibration chips, as described above. Referring to FIG. 12, at step 370 the detectors 66a–66d, 70a–70d are read with the light sources 64, 68 turned off. At step 372, the light sources 64, 68 are turned on, and at step 374 the detectors 66a–66d, 70a–70d are read with the light sources 64, 68 turned on.

If the detector readings taken at steps 370 and 374 are okay as determined at step 376 (e.g. if they are within expected ranges), the routine branches to step 378 where the readings are stored in memory. The magnitudes of the signals generated by the detectors 66a–66d, 70a–70d, with the light sources 64, 68 off are referred to as "dark values," and the magnitudes of the signals generated by the detectors 66a–66d, 70a–70d, with the light sources 64, 68 turned on are referred to as "calibration values." If the detector readings are not acceptable as determined at step 376, the routine branches to step 380 where an error flag is set.

Read Strip Routine

After the dark values and calibration values are determined as described above, the readheads 60, 62 are moved in a direction parallel to the lengths of the reagent strips 14 (or single strip) disposed at the two inspection locations so that the detectors 66a–66d generate illumination signals for each of the reagent pads 26 disposed along the length of each of the reagent strips 14.

This process may be accomplished in the particular manner described below in connection with FIG. 13, which could be used if the motor 58 used for the readhead positioning system described above is a stepping motor, which requires periodic inputs at well-defined intervals to keep the stepping motor running smoothly. The method of FIG. 13 takes a set of detector readings for each of the readheads 60, 62 each time the readheads 60, 62 move a predetermined distance, such as 0.017 of an inch.

Figure 13:
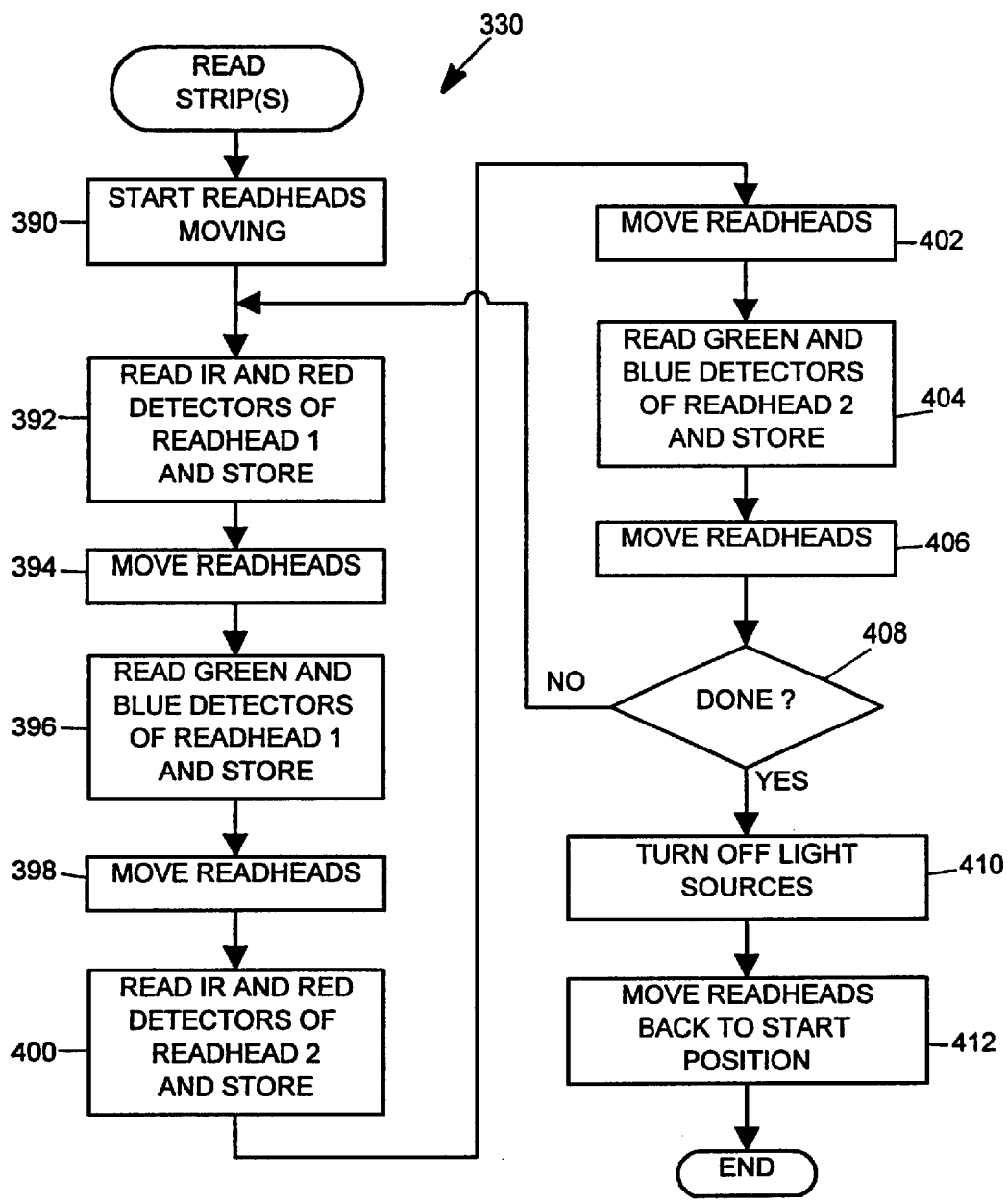
FIG. 13 is a flowchart of a read software routine performed during operation of the spectrophotometer.

Referring to FIG. 13, at step 390 the readheads 60, 62 are started moving, and when they reach a steady-state speed, at step 392 two of the four detectors 66a–66d, for the readhead 60 are read and the signals are stored in memory. At step 394, another drive signal is transmitted to the motor 58 which drives the readheads 60, 62 to cause them to continue moving. At step 396, the other two detectors 66a–66d for the readhead 60 are read and the signals are stored in memory, and at step 398, another drive signal is transmitted to the motor 58 to cause the readheads 60, 62 to continue moving. Even steps 400–406 are performed to cause the detectors 70a–70d of the readhead 62 to be read and the associated signals to be stored in memory, and to drive the motor 58 for the readheads 60, 62.

At step 408, if not all of the desired readings have been taken (which may be determined by keeping track of the distance the readheads 60, 62 have travelled during the read routine 330), the routine branches back to step 392 to get another set of detector readings. If all of the readings have been taken, the routine branches to step 410, where the light sources 64, 68 are turned off, and then to step 412 where the readheads 60, 62 are moved back to their starting position (which is over the calibration chips).

The particular manner of generating the detector readings described in connection with FIG. 13 is not considered necessary to the invention, and other ways of generating the detector readings could be utilized.

Numerous other modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent is:

1. An apparatus for automatically detecting the presence of a reagent strip (14) and for inspecting said reagent strip (14) after the presence of said reagent strip (14) is detected, said apparatus comprising:
    a detection system adapted to automatically detect the presence of a reagent strip (14) at a reagent strip receiving area (12) associated with said apparatus, said detection system comprising:
        a light emitting apparatus (30) adapted to illuminate said reagent strip receiving area (12);
        a detecting apparatus (32) adapted to receive light from said reagent strip receiving area (12) while said reagent strip receiving area (12) is being illuminated by said light emitting apparatus (30) and to generate a detection signal relating to the amount of light detected from said reagent strip receiving area (12); and
        a circuit (120 or 144, 148) adapted to automatically determine whether a reagent strip (14) is present at said reagent strip receiving area (12) based on the magnitude of said detection signal;
    a light source (64 or 68) adapted to illuminate said reagent strip (14) after said circuit (120 or 144, 148) determines the presence of said reagent strip (14) at said reagent strip receiving area (12), said light source (64 or 68) illuminating said reagent strip (14) at an inspection area different from said reagent strip receiving area (12); and
    a detector (66 or 70) adapted to receive light from said reagent strip (14) when said reagent strip (14) is being illuminated by said light source (64 or 68).

2. An apparatus as defined in claim 1 wherein said light emitting apparatus (30) comprises a plurality of light emitting diodes spaced to illuminate separate portions of said reagent strip receiving area (12) and wherein said light detecting apparatus (32) comprises a plurality of light detectors spaced to detect light from a plurality of separate portions of said reagent strip receiving area (12).

3. An apparatus as defined in claim 1,
    wherein said light emitting apparatus (30) comprises a plurality of light emitting diodes spaced to illuminate separate portions of said reagent strip receiving area (12),
    wherein said light detecting apparatus (32) comprises a plurality of light detectors spaced to detect light from a plurality of separate portions of said reagent strip receiving area (12), and
    wherein said light emitting diodes are periodically activated to periodically illuminate said separate portions of said reagent strip receiving area (12).

4. An apparatus as defined in claim 1 wherein said light emitting apparatus (30) is adapted to sequentially illuminate different portions of said reagent strip receiving area (12) at different times.

5. An apparatus as defined in claim 1 wherein said reagent strip (14) has a width and wherein said light emitting apparatus (30) is adapted to illuminate a reagent strip receiving area (12) having a width at least about five times said width of said reagent strip (14).

6. An apparatus as defined in claim 1 wherein said detector (66 or 70) comprises four detectors, each of which detects light of a different wavelength.

7. An apparatus as defined in claim 1 wherein said circuit (120 or 144, 148) is adapted to automatically determine whether a reagent strip (14) is present at said reagent strip receiving area (12) based on a comparison of the magnitude of said detection signal with a threshold.

8. An apparatus as defined in claim 1 wherein said circuit (120 or 144, 148) comprises a controller (120) having a microprocessor (122).

9. An apparatus for automatically detecting the presence of a reagent strip (14) and for inspecting said reagent strip (14) after the presence of said reagent strip (14) is detected, said apparatus comprising:
    a detection system adapted to automatically detect the presence of a reagent strip (14) at a reagent strip receiving area (12) associated with said apparatus, said detection system comprising:
        a light emitting apparatus (30) adapted to illuminate said reagent strip receiving area (12);
        a detecting apparatus (32) adapted to receive light from said reagent strip receiving area (12) while said reagent strip receiving area (12) is being illuminated by said light emitting apparatus (30) and to generate a detection signal having a magnitude that increases with the amount of light detected from said reagent strip receiving area (12); and
        a circuit (120 or 144, 148) adapted to automatically determine that a reagent strip (14) is present at said reagent strip receiving area (12) in the event that the magnitude of said detection signal exceeds a threshold;
    a light source (64 or 68) adapted to illuminate said reagent strip (14) after said circuit (120 or 144, 148) determines the presence of said reagent strip (14) at said reagent strip receiving area (12), said light source (64 or 68) illuminating said reagent strip (14) at an inspection area different from said reagent strip receiving area (12); and
    a detector (66 or 70) adapted to receive light from said reagent strip (14) when said reagent strip (14) is being illuminated by said light source (64 or 68).

10. An apparatus as defined in claim 9 wherein said light emitting apparatus (30) comprises a plurality of light emitting diodes spaced to illuminate separate portions of said reagent strip receiving area (12) and wherein said light detecting apparatus (32) comprises a plurality of light detectors spaced to detect light from a plurality of separate portions of said reagent strip receiving area (12).

11. An apparatus as defined in claim 9,
wherein said light emitting apparatus (30) comprises a plurality of light emitting diodes spaced to illuminate separate portions of said reagent strip receiving area (12),
wherein said light detecting apparatus (32) comprises a plurality of light detectors spaced to detect light from a plurality of separate portions of said reagent strip receiving area (12), and
wherein said light emitting diodes are periodically activated to periodically illuminate said separate portions of said reagent strip receiving area (12).

12. An apparatus as defined in claim 9 wherein said light emitting apparatus (30) is adapted to sequentially illuminate different portions of said reagent strip receiving area (12) at different times.

13. An apparatus as defined in claim 9 wherein said reagent strip (14) has a width and wherein said light emitting apparatus (30) is adapted to illuminate a reagent strip receiving area (12) having a width at least about five times said width of said reagent strip (14).

14. An apparatus as defined in claim 9 wherein said circuit (120 or 144, 148) is adapted to automatically determine whether a reagent strip (14) is present at said reagent strip receiving area (12) based on a comparison of the magnitude of said detection signal with a threshold.

* * * * *